United States Patent
Chen et al.

(10) Patent No.: US 11,771,087 B2
(45) Date of Patent: Oct. 3, 2023

(54) PREPARATION METHOD OF ANTIBACTERIAL DEODORIZING MODIFIED FIBER FOR WATER PURIFICATION

(71) Applicant: Beijing Hongming Xinda Technology Co., Ltd., Beijing (CN)

(72) Inventors: Tao Chen, Beijing (CN); Zhongda Duan, Beijing (CN)

(73) Assignee: Beijing Hongming Xinda Technology Co., Ltd., Beijing (CN)

( * ) Notice: Subject to any disclaimer, the term of this patent is extended or adjusted under 35 U.S.C. 154(b) by 346 days.

(21) Appl. No.: 17/061,134

(22) Filed: Oct. 1, 2020

(65) Prior Publication Data

US 2021/0015099 A1    Jan. 21, 2021

(30) Foreign Application Priority Data

Feb. 26, 2020   (CN) .......................... 202010120501.9

(51) Int. Cl.
| | | |
|---|---|---|
| A01N 43/40 | (2006.01) | |
| A01N 25/34 | (2006.01) | |
| A61L 9/012 | (2006.01) | |
| C02F 1/48 | (2023.01) | |
| A61L 101/48 | (2006.01) | |

(52) U.S. Cl.
CPC .............. *A01N 43/40* (2013.01); *A01N 25/34* (2013.01); *A61L 9/012* (2013.01); *C02F 1/48* (2013.01); *A61L 2101/48* (2020.08); *C02F 2303/02* (2013.01); *C02F 2303/04* (2013.01)

(58) Field of Classification Search
None
See application file for complete search history.

*Primary Examiner* — Erin E Hirt

(57) ABSTRACT

A preparation method of an antibacterial deodorizing modified fiber for water purification is provided. Maleic anhydride is used to perform an addition reaction with sodium polysulfide to generate a disulfide antibacterial agent I, the disulfide antibacterial agent I continues to react with 2-amino-5-nitropyridine in an acetic acid solution under the catalysis of sodium acetate to obtain a compound II, then, the nitro in the compound II is reduced into amino by ferrous sulfate, meanwhile, anhydride is hydrolyzed into carboxylic acid in a faintly acid aqueous solution to obtain a compound III, and finally, under alkaline conditions, the amino in the compound III reacts with the cyan in a polyacrylonitrile fiber to obtain a modified polyacrylonitrile fiber. The prepared modified polyacrylonitrile fiber can remove various heavy metals in sewage and has good antibacterial and anti-mildew effects, thereby achieving the effects of water purification and deodorization.

9 Claims, No Drawings

PREPARATION METHOD OF ANTIBACTERIAL DEODORIZING MODIFIED FIBER FOR WATER PURIFICATION

CROSS REFERENCE TO RELATED APPLICATION

This application claims priority of the Chinese Patent Application filed on Feb. 26, 2020, with the application number of 202010120501.9, and the title of "Preparation Method of Antibacterial Deodorizing Modified Fiber for Water Purification", the entire contents of which are fully incorporated herein by reference.

TECHNICAL FIELD

The present invention belongs to the technical field of environmental protection, and particularly relates to a preparation method of an antibacterial deodorizing modified fiber for water purification.

BACKGROUND

In recent years, with the continuous acceleration of industrialization process, textiles, metal processing and other industries have caused serious water pollution, resulting in the presence of a large number of heavy metal ions and organic pollutants in water bodies, which seriously affects people's life and natural environment. At present, carbon fiber materials are relatively mature in the application of fiber materials in water treatment carriers. Due to the high biological affinity of carbon fibers, active biofilms can be formed, and the microorganisms can be used to decompose the pollutants. The carbon fiber is an ideal biological carrier with a good use effect, it has been widely concerned at home and abroad, and there are many successful engineering application cases. However, although the carbon fiber has good performance, it has a high price and low cost performance, and thus cannot be widely accepted by the market.

The polyacrylonitrile (PAN) fiber is one of the three major synthetic fibers, it has good mechanical strength, thermal stability and chemical resistance, and the raw materials are easily available. However, the polyacrylonitrile does not have the function of purifying water.

SUMMARY OF THE INVENTION

The present invention provides a preparation method of an antibacterial deodorizing modified fiber for water purification. The method is scientific and reasonable, the prepared modified polyacrylonitrile fiber by the present method can remove various heavy metals in sewage and has good antibacterial and anti-mildew effects at the same time, thereby achieving the effects of water purification and deodorization.

The method provided by the present invention includes the following technical solutions:

The method of preparing the antibacterial deodorizing modified fiber for water purification comprises the following steps:

Step 1: preparation of a disulfide antibacterial agent

Step 1.1: preparation of a $Na_2S_x$ solution

Weighing 1 mol of sodium sulfide and 1.5 mol of elemental sulfur, placing the sodium sulfide and the elemental sulfur in a beaker, adding 200 ml of water, heating to 50-60° C., stirring to completely dissolve the sodium sulfide and the elemental sulfur, and cooling to room temperature to obtain the $Na_2S_x$ solution for future use, wherein the x in $Na_2S_x$ is a number of 2-6;

Step 1.2: preparation of a disulfide antibacterial agent I

Weighing 2 mol of sodium bicarbonate, adding the sodium bicarbonate into a reaction bottle, adding 2 L of water, stirring to completely dissolve the sodium bicarbonate, adding 2 mol of maleic anhydride, moving the reaction bottle into an ice salt bath, dripping the $Na_2S_x$ solution prepared in step 1.1 while stirring, removing the reaction bottle from the ice salt bath after the $Na_2S_x$ solution is dripped, continuing to stir for 4-5 h at the room temperature of 20-30° C., performing liquid separation, removing the aqueous solution, adding 1 L of 1 mol/L sodium sulfite solution into the crude product solution, heating to 50° C., continuing to stir to perform the reaction for 2-3 h, performing liquid separation, washing the obtained product with water, and obtaining the disulfide antibacterial agent having the structure of formula I (as shown below) after distillation, wherein the reaction formula is as follows:

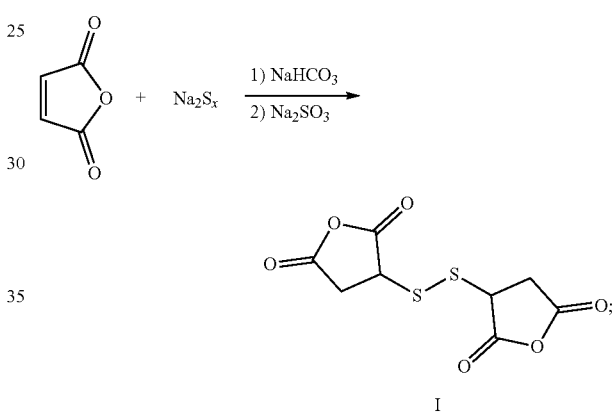

Step 2: introduction of a pyridine chelating group

Adding the disulfide antibacterial agent I prepared in step 1, 1 mol of 2-amino-5-nitropyridine, 1 g of catalyst and 15 ml of acetic acid into the reaction bottle in turn, heating to 115-120° C., stirring to perform the reaction for 4-5 h, performing reduced pressure distillation to remove acetic acid after the reaction is completed, and performing washing, filtering and drying to obtain a compound II, wherein the reaction formula is as follows:

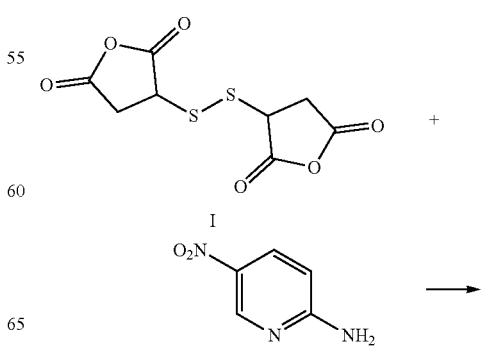

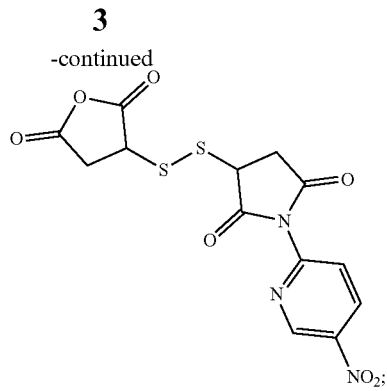

II

Step 3: reduction of the compound II

Adding the compound II prepared in step 2 into a three-necked flask provided with a thermometer, a mechanical stirrer and a reflux condensing tube, adding 100 ml of ethanol aqueous solution with mass fraction of 50%, adjusting the pH of the solution to faintly acid, maintaining the temperature in the three-necked flask at 30-35° C., then adding 0.6 mol of reductant in three batches, that is, adding 0.2 mol of reductant every 20 min, after all the reductant is added, continuing to stir to perform the reduction reaction for 5-6 h, performing recrystallization by using absolute ethyl alcohol after the reaction is completed, and performing filtering and drying to obtain a compound III, wherein the reaction formula is as follows:

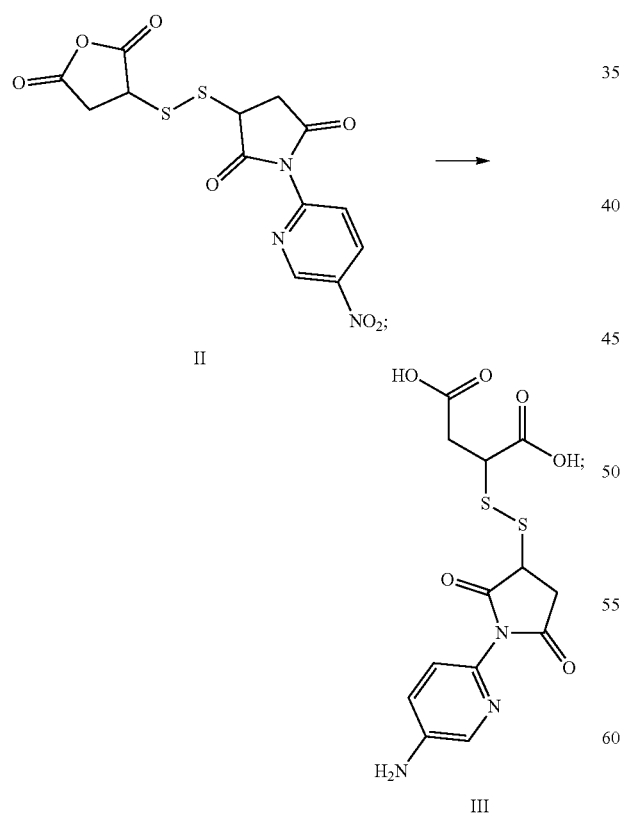

Step 4: modification of polyacrylonitrile fiber

Dissolving the compound III prepared in step 3 in 500 ml of tert-amyl alcohol solution, weighing 1 g of polyacrylonitrile fiber and immersing the same in the tert-amyl alcohol solution, adjusting the pH of the tert-amyl alcohol system to alkalescence, heating up to 120-130° C. to perform a reaction for 4 h to get a primary-treated fiber; taking out the primary-treated fiber after the reaction is completed, washing to neutrality with distilled water, soaking in 0.1 mol/L hydrochloric acid aqueous solution for 3 h to get a secondary-treated fiber; taking out the secondary-treated fiber, washing to neutrality with distilled water, and performing vacuum drying at 50-55° C. for 15-24 h to obtain the modified polyacrylonitrile fiber with the structure shown in formula IV, wherein the reaction formula is as follows:

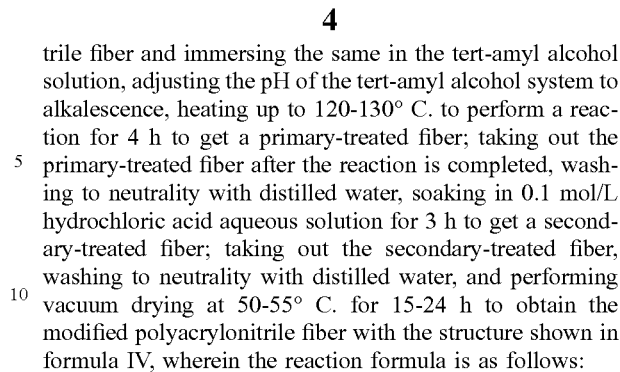

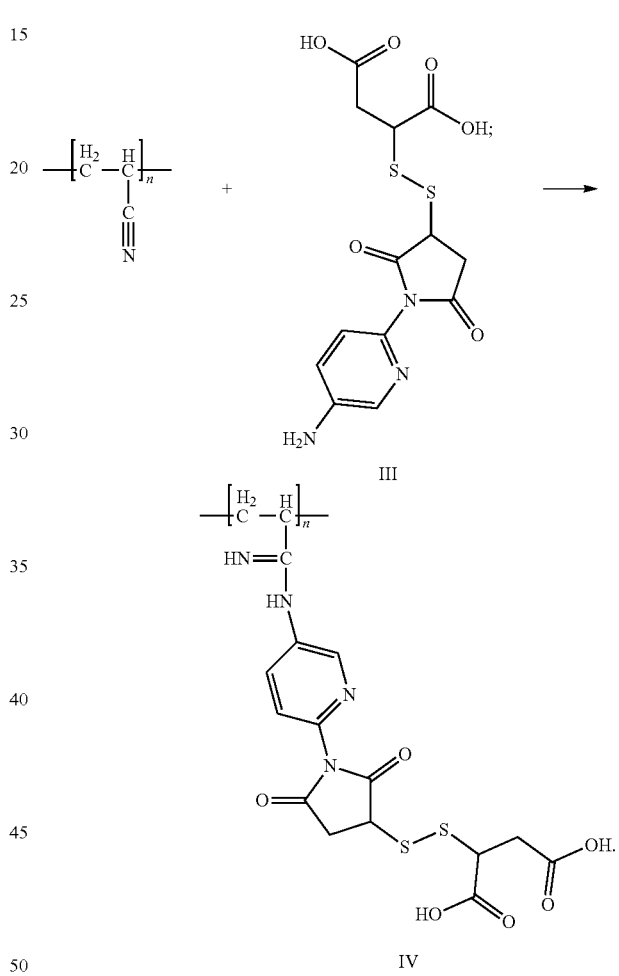

IV

In further embodiments, in step 1.2, the temperature of the ice salt bath is maintained at 0-6° C.

In further embodiments, in step 2, the catalyst is sodium acetate.

In further embodiments, in step 3, adjusting the pH of the solution to faintly acid specifically can be achieved by adjusting the pH of the solution to 5.5-6.2 by using a saturated sodium dihydrogen phosphate aqueous solution.

In further embodiments, in step 3, the reductant is ferrous sulfate.

In further embodiments, in step 4, adjusting the pH of the tert-amyl alcohol system to alkalescence specifically can be achieved by adjusting the pH of the tert-amyl alcohol system to 8.0-8.5 by using a 1 mol/L sodium hydroxide aqueous solution.

The beneficial effects of the present invention include:

The known polyacrylonitrile (PAN) fiber has good mechanical strength, thermal stability and chemical resistance, while does not have the function of purifying water. The inventors of the present invention found that it may because the single structure and lack of functional structure in the polyacrylonitrile.

In the present invention, maleic anhydride is used as a starting material to perform an addition reaction with sodium polysulfide to generate the disulfide antibacterial agent I, the disulfide antibacterial agent I continues to react with 2-amino-5-nitropyridine in the acetic acid solution under the catalysis of sodium acetate to obtain the compound II, the compound II contains an N-pyridine chelating group, and the chelating group can have a chelation with heavy metals in sewage to achieve the purpose of water purification. The nitro in the compound II is then reduced into amino by ferrous sulfate, meanwhile, the anhydride is hydrolyzed into carboxylic acid in a faintly acid aqueous solution to obtain the compound III. Finally, under alkaline conditions, the amino in the compound III reacts with the cyan in the polyacrylonitrile fiber to form imine, thereby introducing two kinds of groups, one is selected from

N-pyridine,

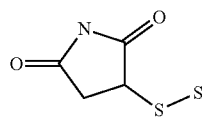

and dicarboxyl, they can provide strong coordination function in the structure of the polyacrylonitrile fiber of the present invention, and the other is selected from disulfide group, pyridyl and carboxylic acid, they can provide antibacterial and anti-mildew properties for the polyacrylonitrile fiber of the present invention. Then the fiber of the present invention can also inhibit harmful bacteria and molds while removing the heavy metal ions in the sewage, thereby achieving the effect of water purification and deodorization. Furthermore, the modified polyacrylonitrile fiber has good desorption and renewable performance, in the mixed acid solution of 1 mol/L hydrochloric acid and 1 mol/L sulfuric acid, 95% of heavy metal desorption can be achieved, and the regenerative modified polyacrylonitrile fiber can be used for many times, so that the utilization rate is higher.

DETAILED DESCRIPTION

A clear and complete description of technical solutions in the embodiments of the present invention will be given below. Apparently, the embodiments described below are merely a part, but not all, of the embodiments of the present invention. All of other embodiments, obtained by those of ordinary skilled in the art based on the embodiments of the present invention without any creative effort, fall into the protection scope of the present invention.

Embodiment 1

The preparation method of an antibacterial deodorizing modified fiber for water purification specifically includes the following steps:

Step 1: preparation of a disulfide antibacterial agent
The reaction formula is as follows:

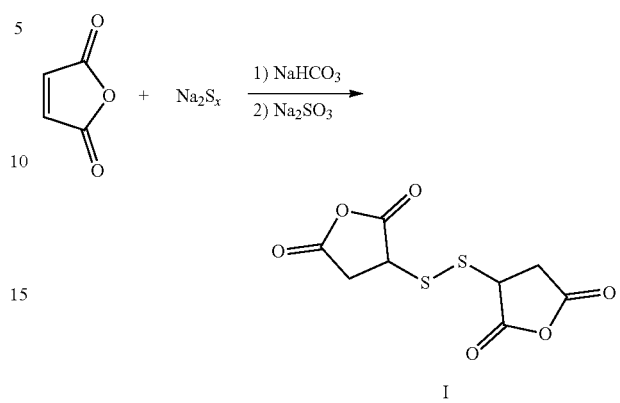

Step 1.1: preparation of a $Na_2S_x$ solution 1 mol of sodium sulfide and 1.5 mol of elemental sulfur were weighed and placed in a beaker, and 200 ml of water was added, the mixture was then heated to 50-60° C., with continuously stirring to completely dissolve the sodium sulfide and the elemental sulfur. The solution was cooled to room temperature to obtain the $Na_2S_x$ solution for future use, wherein the x in $Na_2S_x$ is a number of 2-6;

Step 1.2: preparation of a disulfide antibacterial agent I 2 mol of sodium bicarbonate was weighed and added into a reaction bottle, 2 L of water was added, the mixture was stirred to completely dissolve the sodium bicarbonate, and then 2 mol of maleic anhydride was added. The reaction bottle was moved into an ice salt bath, the temperature of the ice salt bath was maintained at 0-6° C., the $Na_2S_x$ solution prepared in step 1.1 was dripped into the reaction bottle while stirring. After the $Na_2S_x$ solution is dripped, the reaction bottle was removed from the ice salt bath and continuously stirred for 5 h at the room temperature of 25° C., then liquid separation was performed to remove the aqueous solution, 1 L of 1 mol/L sodium sulfite solution was added into the crude product solution, the solution was heated to 50° C. and was continuously stirred to react for 2 h, the liquid separation was performed again, and the product was washed with water, distilled to obtain the disulfide antibacterial agent having the structure of formula I (as shown above);

The mass spectrometry result of the obtained target product I is: HRMS m/z (ESI$^+$) calcd for $C_8H_6O_6S_2([M]^+)$, 261.95, found 261.2621.

Step 2: introduction of a pyridine chelating group
The reaction formula is as follows:

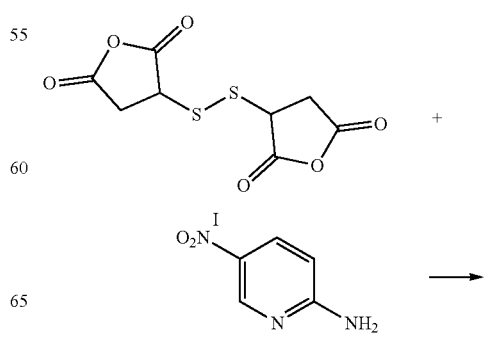

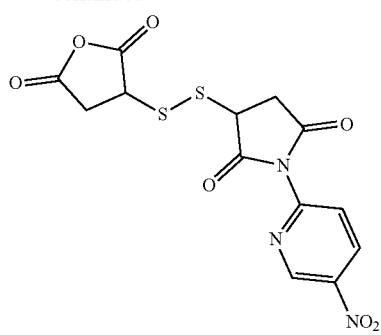

II

The disulfide antibacterial agent I prepared in step 1, 1 mol of 2-amino-5-nitropyridine, 1 g of sodium acetate and 15 ml of acetic acid were added into the reaction bottle in turn, the mixture was heated to 120° C. and stirred to perform the reaction for 4 h, the reduced pressure distillation was then performed to remove acetic acid after the reaction is completed, the sodium acetate was removed by washing with water, and a compound II was obtained by filtering and drying.

The mass spectrometry result of the obtained target product II is: HRMS m/z (ESI$^+$) calcd for $C_{13}H_9N_3O_7S_2([M]^+)$, 383.36, found 382.9924.

Step 3: reduction of the compound II

The reaction formula is as follows:

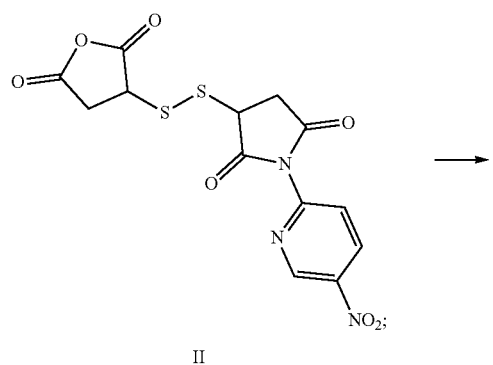

The compound II prepared in step 2 was added into a three-necked flask provided with a thermometer, a mechanical stirrer and a reflux condensing tube, 100 ml of ethanol aqueous solution with mass fraction of 50% was added, and the pH of the solution was adjusted to 5.8 by using saturated sodium dihydrogen phosphate aqueous solution, the temperature in the three-necked flask was maintained at 30° C., then 0.6 mol of reductant was added in three batches, that is, 0.2 mol of reductant was added every 20 min, after all the reductant is added, the reduction reaction was continued for 5-6 h with stirring, then recrystallization was performed by using absolute ethyl alcohol after the reaction is completed, and filtering and drying ware performed to obtain a compound III, the reductant used was ferrous sulfate.

The mass spectrometry result of the obtained target product III is: HRMS m/z (ESI$^+$) calcd for $C_{13}H_{13}N_3O_6S_2([M]^+)$, 371.25, found 371.1279.

The nuclear magnetic characterization of the compound III:

$^1$H NMR (400 MHz, CDCl$_3$): δ11.05 (s, 2H), 8.56 (d, J=7.4 Hz, 1H), 7.65 (s, J=8.6 Hz, 1H), 7.11 (d, J=7.0, 1H), 5.84 (s, 2H), 3.71 (t, 2H), 3.12 (d, 2H), 2.75 (d, 2H) ppm.

Step 4: modification of polyacrylonitrile fiber

The compound III prepared in step 3 was dissolved in 500 ml of tert-amyl alcohol solution, 1 g of polyacrylonitrile fiber was weighed and immersed in the tert-amyl alcohol solution, the pH of the tert-amyl alcohol system was adjusted to 8.5 by using a 1 mol/L sodium hydroxide aqueous solution, the reaction solution was heated up to 130° C. to react for 4 h, the fiber was taken out after the reaction is completed, and washed to neutrality with distilled water, the prepared fiber was soaked in 0.1 mol/L hydrochloric acid aqueous solution for 3 h, the fiber was taken out again and washed to neutrality with distilled water, then vacuum drying was performed at 50° C. for 24 h to obtain the modified polyacrylonitrile fiber with the structure of formula IV (as shown below).

The reaction formula is as follows:

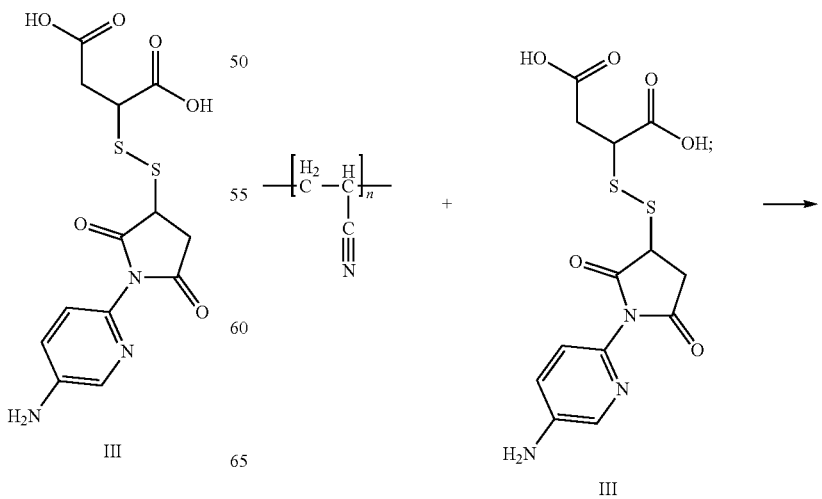

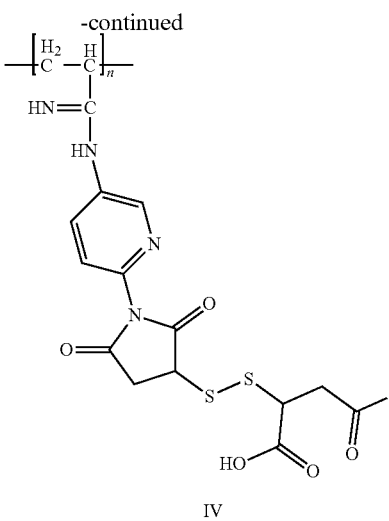

IV

The infrared characterization of the modified polyacrylonitrile fiber D is shown as follows: IR(KBr): $\bar{\nu}$=3315-3449 cm$^{-1}$ (—NH—,—COOH), 3229 cm$^{-1}$ (—C=NH—), 3029 cm$^{-1}$ (pyridine), 1732 cm$^{-1}$ (—CO—), 1655 cm$^{-1}$ (—C=NH—).

The performance test of the modified polyacrylonitrile fiber:

1. Antibacterial property of the modified polyacrylonitrile fiber

In the measurement of the minimum inhibitory concentration (MIC), the minimum concentration of the compound that has obviously aseptically grown in a test tube is the minimum inhibitory concentration of the compound;

TABLE 1

MIC value of the modified polyacrylonitrile fiber

| | Staphylococcus aureus (mg/ml) | Escherichia coli (mg/ml) | Schizosaccharomyces (mg/ml) |
|---|---|---|---|
| Polyacrylonitrile fiber | no antibacterial activity | no antibacterial activity | no antibacterial activity |
| Carbon fiber | 0.254 | 0.158 | 0.173 |
| Modified polyacrylonitrile fiber | 0.034 | 0.067 | 0.095 |

2. Adsorption of heavy metal ions by the modified polyacrylonitrile fiber 10 g of modified polyacrylonitrile fiber and 10 g of carbon fiber were taken respectively, the fibers were added into 600 mL of waste water containing metal ion for 24 h, and the metal ion adsorption capacity was tested by an inductively coupled plasma emission spectrometer. In the waste water containing metal ion, the concentration of iron ions is 1500 ppm, the concentration of copper ions is 1000 ppm, the concentration of lead ions is 800 ppm, the concentration of silver ions is 500 ppm, and the concentration of mercury ions is 400 ppm;

TABLE 2

Adsorption results of the heavy metal ions by the modified polyacrylonitrile fiber

| | Adsorption capacity of iron ions (mg/g) | Adsorption capacity of copper ions (mg/g) | Adsorption capacity of lead ions (mg/g) | Adsorption capacity of silver ions (mg/g) | Adsorption capacity of mercury ions (mg/g) |
|---|---|---|---|---|---|
| Carbon fiber | 402.7 | 228.1 | 189.2 | 89.2 | 110.3 |
| Modified polyacrylonitrile fiber | 532.3 | 318.7 | 226.9 | 148.6 | 159.4 |

The modified polyacrylonitrile fiber and the carbon fiber after adsorption were placed respectively in 10 L of mixed acid solution (1 mol/L hydrochloric acid and 1 mol/L sulfuric acid). 5 h later, the fibers were taken out, washed and dried for 10 h, and repeated the adsorption experiment of the heavy metal ions with the same waste water, and the results are shown in Table 3:

TABLE 3

Adsorption results of the heavy metal ions by regenerated fibers

| | Adsorption capacity of iron ions (mg/g) | Adsorption capacity of copper ions (mg/g) | Adsorption capacity of lead ions (mg/g) | Adsorption capacity of silver ions (mg/g) | Adsorption capacity of mercury ions (mg/g) |
|---|---|---|---|---|---|
| Carbon fiber | 287.3 | 148.6 | 120.7 | 52.4 | 88.8 |
| Modified polyacrylonitrile fiber | 522.0 | 312.6 | 215.8 | 142.4 | 150.7 |

It can be seen from Table 2 and Table 3 that the modified polyacrylonitrile fiber of the present invention has good adsorption for various heavy metals in the waste water, and still has good adsorption capacity for the heavy metal ions after being regenerated.

The above content is only an example and description of the concept of the present invention. Those skilled in the art to which the present invention belongs can make various modifications or supplements to the specific embodiments described or makes substitutes in a similar manner, and all these modifications or supplements or substitutes all belong to the protection scope of the present invention as long as not deviating from the concept of the present invention or exceeding the scope defined in the claims.

We claim:

1. A method of preparing an antimicrobial deodorizing modified fiber for water purification, comprising:

1) preparing a $Na_2S_x$ solution comprising: taking 1 mol of sodium sulfide and 1.5 mol of elemental sulfur, adding into 200 mL of water and heating to 50-60° C., stirring to completely dissolve the sodium sulfide and the elemental sulfur, and cooling to room temperature of 20-30° C. to obtain the $Na_2S_x$ solution, wherein the x in the $Na_2S_x$ is from 2-6;

2) preparing a disulfide antibacterial agent I comprising adding 2 mol of sodium bicarbonate into a reaction bottle, adding 2 L of water, stirring to completely dissolve the sodium bicarbonate; adding 2 mol of maleic anhydride; moving the reaction bottle into an ice salt bath, dripping the $Na_2S_x$ solution from step 1) into the reaction bottle while stirring; removing the reaction bottle from the ice salt bath, and stirring for 4-5 h at room temperature of 20-30° C.; performing liquid separation to remove the aqueous solution and yield a crude product solution; adding 1 L of 1 mol/L sodium sulfite solution into the crude product solution, heating to 50° C., stirring for 2-3 h; performing liquid separation to remove the aqueous solution, and yield a crude disulfide antibacterial agent I which is washed with water; distilling the crude disulfide antibacterial agent I to obtain pure disulfide antibacterial agent I of formula I, via the following reaction formula:

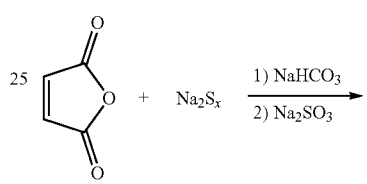

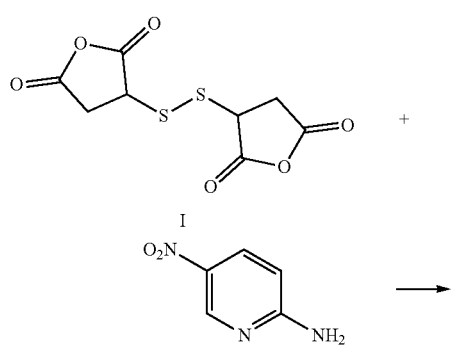

3) introducing a pyridine chelating group comprising adding the disulfide antibacterial agent I from step 2, 1 mol of 2-amino-5-nitropyridine, 1 g of catalyst and 15 ml of acetic acid which forms a reaction mixture; heating to 115-120° C., and stirring for 4-5 h; distilling the reaction mixture under reduced pressure to remove acetic acid, and washing, filtering, and drying the reaction mixture to obtain compound II via the following reaction formula:

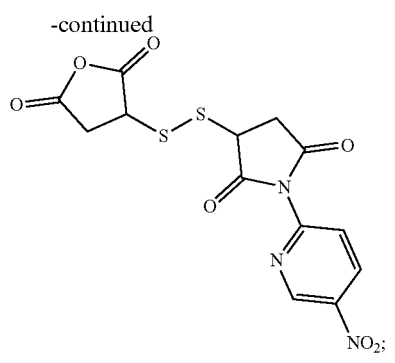

II 4) reducing compound II comprising adding compound II from step 3 and 100 ml of ethanol aqueous solution with mass fraction of 50%, to form a solution, adjusting the pH of the solution to acidic, and maintaining the temperature at 30-35° C., adding 0.6 mol of reductant at a rate of 0.2 mol of reductant every 20 min to the solution to form a reaction mixture; stirring the reaction mixture for 5-6 h; recrystallizing with absolute ethanol; filtering and drying to obtain compound III, via the following reaction formula:

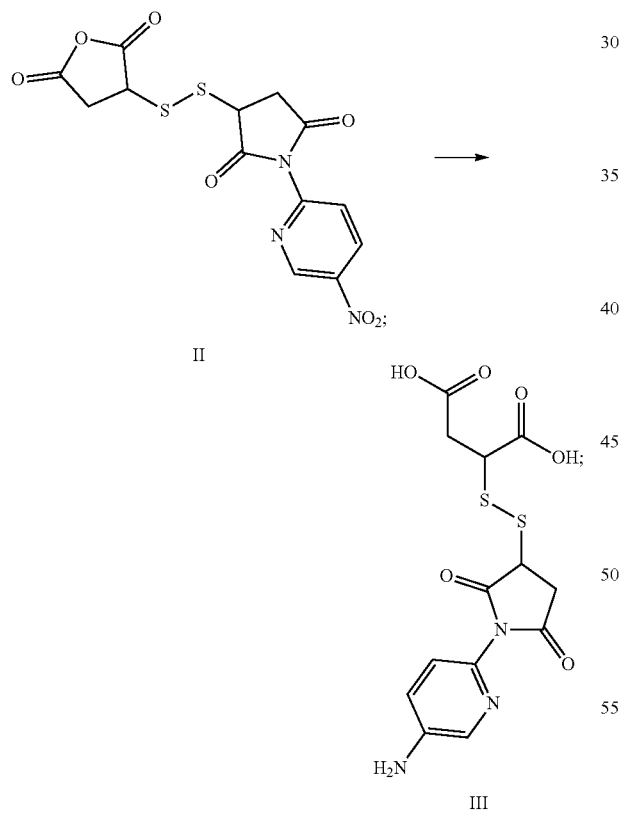

5) modifying polyacrylonitrile fiber comprising dissolving compound III from step 4) in 500 ml of tert-amyl alcohol solution, adding 1 g of polyacrylonitrile fiber and adjusting the pH to alkaline; heating to 120-130° C. for 4 h to form a crude fiber product; removing the crude fiber product and washing with water to neutral pH, soaking the crude fiber product in 0.1 mol/L aqueous hydrochloric acid to form a crude secondary-treated fiber; washing the crude secondary-treated fiber with distilled water to neutral pH, and drying via vacuum at 50-55° C. for 15-24 h to yield the modified polyacrylonitrile fiber of formula IV via the following reaction formula:

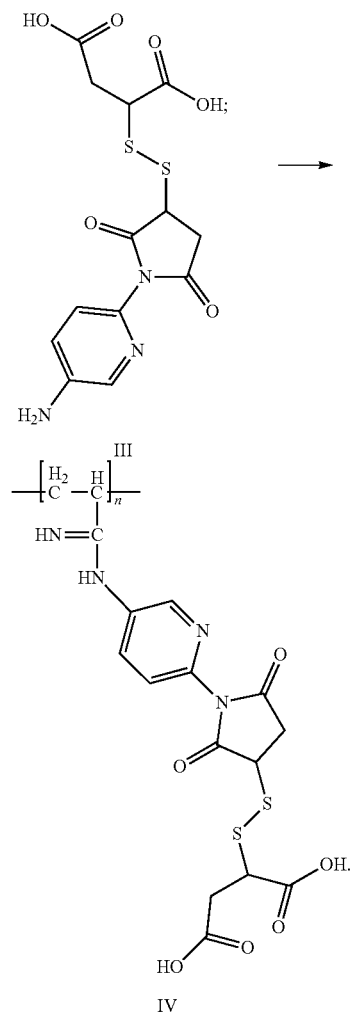

IV

2. The method of preparing the antibacterial deodorizing modified fiber for water purification according to claim 1, wherein, in step 2, the temperature of the ice salt bath is maintained at 0-6° C.

3. The method of preparing the antibacterial deodorizing modified fiber for water purification according to claim 1, wherein, in step 3, the catalyst is sodium acetate.

4. The method of preparing the antibacterial deodorizing modified fiber for water purification according to claim 1, wherein, in step 4, the adjusting of the pH of the solution is to a pH of 5.5-6.2, and the adjusting step is accomplished by adding a saturated sodium dihydrogen phosphate aqueous solution.

5. The method of preparing the antibacterial deodorizing modified fiber for water purification according to claim 1, wherein, in step 4, the reductant is ferrous sulfate.

6. The method of preparing the antibacterial deodorizing modified fiber for water purification according to claim 1, wherein, in step 5, the adjusting of the pH of the solution is to a pH of 8.0-8.5, and the adjusting step is accomplished by adding a 1 mol/L sodium hydroxide aqueous solution.

7. The method of preparing the antibacterial deodorizing modified fiber for water purification according to claim 6, wherein in step 4, the adjusting of the pH of the solution is to a pH of 5.5-6.2, and the adjusting step is accomplished by adding a saturated sodium dihydrogen phosphate aqueous solution adjusting.

8. The method of preparing the antibacterial deodorizing modified fiber for water purification according to claim 7, wherein in step 3, the catalyst is sodium acetate.

9. The method of preparing the antibacterial deodorizing modified fiber for water purification according to claim 8, wherein in step 2, the temperature of the ice salt bath is maintained at 0-6° C.

* * * * *